United States Patent [19]

George et al.

[11] Patent Number: 5,102,549

[45] Date of Patent: Apr. 7, 1992

[54] TREATMENT OF LOWER GLYCOL-CONTAINING OPERATIVE FLUIDS

[75] Inventors: Kathleen F. George, Cross Lanes; Lise Dahuron; John H. Robson, both of Charleston, W. Va.; George E. Keller, II, So. Charleston, all of W. Va.; Benjamin Bikson, Brookline, Mass.

[73] Assignee: Union Carbide Chemicals & Plastics Technology Corporation, Danbury, Conn.

[21] Appl. No.: 654,121

[22] Filed: Feb. 14, 1991

Related U.S. Application Data

[63] Continuation-in-part of Ser. No. 457,923, Dec. 27, 1989, Pat. No. 5,034,134.

[51] Int. Cl.⁵ .................... B01D 61/02; B01D 71/68

[52] U.S. Cl. ............................ 210/639; 210/500.41
[58] Field of Search ............... 210/500.29, 639, 500.41

[56] References Cited

U.S. PATENT DOCUMENTS 3,467,604  9/1969  Michaels ........................... 260/2.5
3,875,096  4/1975  Graefe et al. .................... 260/29.2
4,851,120  7/1989  Reineke et al. ................ 210/500.29

Primary Examiner—Frank Sever
Attorney, Agent, or Firm—Jean B. Mauro

[57] ABSTRACT

Operative fluids containing lower glycol are contacted with semi-permeable membranes under reverse osmosis conditions to permeate lower glycol to provide a reclaimed lower glycol product. Exemplary operative fluids include antifreeze solutions, heat transfer fluids, deicers, quenchants, hydraulic fluids, lubricants, solvents and absorbents.

9 Claims, No Drawings

TREATMENT OF LOWER GLYCOL-CONTAINING OPERATIVE FLUIDS

This is a continuation-in-part of U.S. patent application Ser. No. 457,923, filed Dec. 27, 1989, now U.S. Pat. No. 5,034,134, herein incorporated by reference.

This invention pertains to processes for reclaiming lower glycol from operative fluids containing lower glycol, especially used operative fluids. The processes of this invention may provide reclaimed lower glycol of sufficient quality that the lower glycol may be suitable for reuse in operative fluids.

BACKGROUND OF THE INVENTION

Lower glycols, i.e., monoethylene glycol 1,2-propylene glycol and 1,3 propanediol, find a plurality of uses as operative fluids, e.g., antifreezes, deicers, heat transfer fluids, quenchants, brake fluids and other hydraulic fluids, lubricants, absorbents, and solvents. Operation fluids are thus characterized as fluids which are used to perform a function. In the context of performing this function, they are subjected to inclusion of impurities and/or degradation. For instance, an antifreeze composition for an internal combustion engine may not only be subject to heat, but also to the various materials of construction of the cooling system as well as dirt, combustion gases in the event of leaky heat gaskets, and the like.

Often operative fluids contain corrosion inhibitors, buffers, antioxidants and/or other adjuvants to make them suitable for use in process equipment. These adjuvants may be consumed or removed from the fluid during use. Contamination of the fluids may also occur during use or storage, and the fluids, especially those subjected to elevated temperatures, may degrade. The degradation products may be deleterious in the process equipment in which the operative fluid is used. With the loss of the adjuvant effectiveness or upon contamination or upon the generation of undue amounts of degradation products, the operative fluid may become unacceptable for its intended use.

When the operative fluid becomes unacceptable for its intended use, the fluid has frequently been disposed. Not only does this entail a loss of lower glycol values, but, also, care should be taken to assure that the manner of disposal of the fluid is environmentally acceptable. Alternatively, the lower glycol could be recovered from the operative fluid for reuse. Separation processes, such as distillation of spent solvents, can prove to be energy intensive. See, for instance, *Chemical Abstracts*. Vol. 111 (20); 177607 q, summarizing Shub, et al., "Utilization of Used Antifreeze", *Khim. Tekhnol. Topl. Masel* (8), 16–18 (1989); U.S. Pat. No. 4,225,394; *Chemical Abstracts*, Vol 101(4): 25944 c, summarizing Hungarian patent publication 29752, Feb. 28, 1984; and *Chemical Abstracts*, Vol. 104 (22): 189629 s, summarizing Wehner, et al., "Processing of Residues from Solvent Regeneration for Selective Separation Processes", East German patent number 226557, Aug. 28, 1985.

U.S. Pat. No. 4,427,507 discloses an electrodialysis system for recovering ethylene glycol from aqueous purge streams for ethylene oxide plants. The patentees state:

"Finally, the process according to the invention might also be used in the regeneration of glycol-water antifreeze mixtures for instance for motor cars." (Column 4, lines 13 to 15)

No example or statement relating to the effectiveness of electrodialysis for recovery of ethylene glycol from antifreeze mixtures is given. In view of the inability of electrodialysis to effect separation of non-charged components such as colloidal metals and organic contaminants, the viability of electrodialysis as an effective means to recover glycol from antifreeze mixtures is placed into question. *Chemical Abstracts*, Vol. 104 (20): 170054d, reporting on Japanese patent application Kokai 60/216884, Oct. 30, 1985, relates that electrodialysis has been proposed to treat waste water from polyester fiber manufacturing. No disclosure or suggestion of the use of electrodialysis for recovery of ethylene glycol from antifreeze is reported.

British patent specification No. 1,463,324 discloses the use of semi-permeable membranes for the recovery of ethylene glycol from waste water for ethylene oxide processes. A commercial polyamide membrane made by duPont was the only specified membrane and membrane material.

Grunwald's Czech patent application 87/01681 is reported by Derwent, 88-315268/45, to disclose waste antifreeze regeneration by removing mechanical impurities, passing the material through cation exchanger and adding ethylene or propylene glycol.

As another alternative to the recovery of lower glycol, operative fluid for some applications can be analyzed, and appropriate adjuvants in appropriate amounts can be added to the operative fluids to replenish adjuvants or counter at least some of the effects of degradation products or contaminants. This procedure is frequently not practical except in large scale industrial applications. Without an analysis, a risk exists that too much or too little of the adjuvant or that an improper adjuvant may be added to the fluid. In such an event, the deleterious properties of the operative fluid may not be sufficiently ameliorated, and even may be exacerbated, by the improper concentrations of adjuvants. Moreover, the presence of contaminants is not addressed by the addition of adjuvants.

Accordingly, processes are sought which can effectively reclaim lower glycol from operative fluids such that deleterious contaminants and degradation products, whether or not ionic, can be removed and such that any adjuvants, whether in active or consumed form, can be removed. The reclaimed lower glycol can then, for instance, be reused as an operative fluid and a standard adjuvant package added without the need for analysis. Advantageously, the processes would be economical, require little energy consumption and be reliable.

The benefits of such processes would not only be perceptible for industrial applications such as heat transfer fluids, quenchants and absorbents, but also would apply to small applications such as local processing of used automotive antifreeze. Further, the processes may be viable for deicing utilities such as for aircraft and airport runways where on-site processing of intermittent, large quantities of operative fluid is sought.

SUMMARY OF THE INVENTION

By this invention, processes are provided for reclaiming lower glycol (one or more of monoethylene glycol, 1,2-propylene glycol and 1,3-propane diol) from operative fluids. The processes can effectively remove adjuvants such as corrosion inhibitors, buffers, antioxidants and the like from the ethylene glycol as well as contaminants, including nonionic organic contaminants and colloidal metals, and many glycol degradation products such as acids and some esters of lower glycol. In the processes of the invention, the operative fluid is contacted with a feed side of a semi-permeable membrane and, on a permeate side of the membrane, a permeate having lower glycol of enhanced purity is obtained. The semi-permeable membrane is characterized as (a) being capable of rejecting at least about 70 percent of sodium chloride contained in a 3.5 weight percent aqueous solution at 25° C. and 1000 pounds per square inch pressure drop across the membrane with 20 volume percent recovery of water ("Standard Conditions");

(b) being capable of rejecting less than about 30 percent of monoethylene glycol contained in a 10 weight percent aqueous solution at Standard Conditions; and (c) being capable of rejecting at least about 90 weight percent of an eight mole ethoxylate of nonylphenol having an average molecular weight of about 570 contained in a 1.0 weight percent aqueous solution at Standard Conditions. Hence, the processes of this invention are attractive for recovery of lower glycols from operative fluids. The reverse osmosis membrane separation is effective for removing a wide variety of components that may be present in operative fluids including ionic and non-ionic components such as hydrocarbons (oils, fuels, polymers, etc.); ethers and polyethers (glycol ethers, polyethylene glycols, higher glycols such as tetraethylene glycols); acids; esters; amines; silicones; salts (halides, acetates, phosphates, borates, silicates, etc.); colloidal metals; dyes; and the like.

In a preferred aspect of the invention, the membrane is operated such that at least about 20 weight percent of the lower glycol in the spent solvent or operative fluid is permeated through the membrane. Often, the electroconductivity of the permeate is less than about 50 percent of the electroconductivity of the spent solvent or operative fluid prior to contact with the membrane.

In another preferred aspect of this invention, the membrane comprises a polymer containing anionic pendant groups. The anionic groups include, but are not limited to, one or more of carboxylic, sulfonic, sulfinic, phosphonic, phosphinic, etc., groups. Often, the anionic groups are present in a concentration such that the ion exchange capacity of the membrane is from about 0.01 to about 3 milliequivalents per gram of dry polymer, preferably from about 0.5 to about 2 milliequivalents per gram of dry polymer.

In a further preferred aspect of this invention, the membrane comprises polysulfone, and, most preferably, sulfonated polysulfone.

In an aspect of the invention, membranes which are adversely affected by lower glycol can be employed by maintaining the concentration of lower glycol on the feed side of the membrane below that which would deleteriously affect the semi-permeable membrane, i.e., often below about 80 volume percent based on the volume of fluid on the feed side of the membrane. In this aspect of this invention, it may sometimes be convenient to provide sufficient diluent, e.g., water, to the spent solvent or operative fluid on the feed side of the membrane to assure that the membrane is not unduly deleteriously affected.

In a separate aspect of the invention, the stability of membranes for separation of liquids, especially membranes containing anionic pendant groups, is enhanced by periodically or continuously contacting the membrane with a stabilizing amount of di- or polyvalent cation, preferably divalent cation especially alkaline earth metal cation. The stabilizing cation should be sufficiently soluble in the medium in which it is contained for contact with the membrane such that the stabilizing effects can be achieved. Often, the membrane treating solution is at least about 0.01 Normal with respect to the treating salt and the concentration of the salt is less than the saturation concentration at the conditions of the treating, often, the solution is between about 0.1 and 2 Normal.

DETAILED DESCRIPTION

Exemplary of the operative fluids containing lower glycol from which lower glycol may be sought to be reclaimed include antifreeze compositions for mobile and stationary water-cooled engines, e.g., for automobiles, trucks, buses, and generators; deicers; heat transfer fluids, e.g., for stationary power plants; quenchants, e.g., for molten metals; hydraulic fluids; lubricants, absorbents, especially regenerable absorbents, and solvents. Solvent uses for lower glycol include pharmaceutical and other chemical and biochemical processes.

Operative fluids often contact metal or other potentially corrodible surfaces. Hence, corrosion inhibitors are frequently provided in the fluids. Corrosion inhibitors include phosphates, borates, silicates, tungstates, molybdates, benzoates, nitrites, benzotriazole, tolyltriazole, mercaptobenzothiazole, arsenites, and the like. Buffers, e.g., to a pH of about 7.5 to 9.0, are also often present to enhance the performance of the corrosion inhibitors and to neutralize typically acidic degradation products of ethylene glycol. Antioxidants, foam inhibitors, and surfactants may also be present in operative fluids. Frequently, the adjuvants are consumed during the use of the fluid or are eliminated from the operative fluid through, e.g., evaporation or through selective contact with articles contacting the operative fluid such as with cooled metal removed from quenchant baths.

Contaminants in operative fluids may vary widely from those which may be encountered by contact with materials in closed loop heat transfer systems, e.g., metal degradation and abrasion products, to those which occur via intrusion through leaky seals, e.g., in internal combustion engines, to those such as may be present on the material contacted by the operative fluid such as ground contaminants contacting deicing fluids. Hence, the contaminants may be organic or inorganic. Degradation products typically include esters and acids such as ethylene glycol diacetate, ethylene glycol monoacetate, acetic acid and the like for ethylene glycol-based operative fluids and homologous products for propylene glycol-based fluids.

In accordance with the invention, the operative fluid is contacted with a feed side of a semi-permeable membrane under reverse osmosis conditions sufficient to permeate lower glycol to the permeate side of the membrane. If water is present, at least a portion of the water permeates with the lower glycol. The membrane, however, must reject sufficient proportions of species sought to be removed from the feed stream so that a permeate of enhanced purity is obtained. To obtain desirable purity enhancement, the membranes, under Standard Conditions, are capable of rejecting at least about 70 percent of the sodium chloride in a 3.5 weight percent aqueous solution. Often, this rejection is between about 90 and 99.9 percent, say about 90 to 99.5 percent. The rejection percentage as used herein refers to the quotient of (i) the quantity of the concentration of the component in the feed less the concentration of that component in the permeate divided by (ii) the concentration of that component in the feed. The membrane should also exhibit suitable selectivity of separation in respect of organic components in the operation fluid. The rejection of ethoxylate of nonylphenol having an average molecular weight (molecular weight average) of about 570 is at least about 90 weight percent, preferably at least about 95, often about 97 to 99.9, weight percent, when contained in a 1.0 weight percent aqueous solution at Standard Conditions. The ethoxylate is prepared by base catalyzed ethoxylation of nonylphenol and thus exists as a mixture of ethoxylated species. A suitable nonylphenol ethoxylate is available as NP-8 from Union Carbide Chemicals and Plastics Company Inc. Danbury, Conn., United States of America.

It is recognized that membranes which are operable and contemplated for use in accordance with the present invention may not be able to withstand pressure drops of 1000 pounds per square inch as set forth for Standard Conditions. In such event, alternative Standard Conditions are employed which involve a 200 pound per square inch pressure drop across the membrane. With these alternative Standard Conditions, the concentration of sodium chloride to determine sodium chloride rejection is 1100 parts per million by weight instead of 3.5 weight percent. All other test conditions are the same.

Desirably, not only does the semi-permeable membrane exhibit adequate separation properties to reclaim lower glycol but also the membrane should exhibit sufficient chemical resistance to lower glycol that the membrane is not unduly deleteriously affected during the separation process. Because of the strong solvating properties of lower glycol, some polymeric membranes are subject to being adversely affected by contact with lower glycol. By aspects of this invention, preferred membrane structures, polymer compositions and/or operating procedures can be employed to enhance the operability of the use of membranes to reclaim lower glycol.

Composite membranes are preferred membrane structures. Composite membranes comprise a thin membrane coating on a porous support. The porous support may be fabricated from material which may not have the sought separation properties but which may have desirable strength and chemical resistance properties. Another type of membrane structure that may find application is anisotropic or asymmetric membranes comprised essentially of a single permeable membrane material distinguished by the existence of two distinct morphological regions within the membrane structure. One region comprises a thin, relatively dense semi-permeable skin capable of selectively permeating one component of a fluid mixture. The other region comprises a less dense, porous, non-selective support region that serves to support the collapse of the thin skin region of the membrane under pressure.

Membranes may be fabricated in various shapes and produced in various assemblies, such as (1) a flat sheet which may be supported in a typical plate and frame structure similar to a filter press; (2) a flat sheet rolled into spirals with spacing materials interleaved with the membrane and the assembly sealed to provide spiroidal channels permitting the passage of the feed on one side of the coiled membrane to the opposite side of the membrane; (3) as tubes lining the inner surface of a reinforced braid, the braid itself at times being a component in a larger tube; or (4) in the form of open-ended hollow fibers so organized and sealed into header plates so as to provide a separation of the flow over the external surfaces of the hollow fibers from any flow within the bores of the hollow fibers ensuing by virtue of passage of the liquid feed mixture across the membrane.

Hollow fiber membranes are often used in the process of the invention. Frequently, the hollow fibers may have outside diameters of about 20 to 1,000 microns, generally about 50 to 500 microns, and have walls of at least about 5 microns in thickness, generally about 50 to about 450 microns thick. The wall thickness in some hollow fibers may be up to about 200 or 300 microns. The membrane coating may have a thickness ranging from about 0.01 to about 10 microns and preferably has a thickness of about 0.05 to about 2 microns. In order to provide desirable fluxes through the hollow fibers, particularly using those hollow fibers having walls at least about 50 microns in thickness, the hollow fibers may have a substantial void volume. Voids are regions within the walls of the hollow fibers which are vacant of the material of the hollow fibers. Often, when voids are desired, the void volume of the hollow fibers is up to about 90, generally about 10 to 80, and sometimes about 20 or 30 to 70, percent based on the superficial volume, i.e., the volume contained within the gross dimensions, of the hollow fiber. The dense layer in anisotropic membranes or the membrane coating layer in composite membranes is relatively thin to permit suitable permeate flux rates. The thickness of the dense layer or membrane coating, as the case may be, is often from about 0.01 to about 10 microns, preferably, between about 0.05 to about 2 microns.

Although the foregoing description has been directed to hollow fiber membranes, film membranes often share structural characteristics.

The material used for the membrane may be a solid, natural or synthetic substance. The selection of the material for the membrane may be based on the heat resistance and/or mechanical strength of the membrane, as well as other factors dictated by the separation process of the present invention and the operating conditions to which it will be subjected. The materials used, whether it be the porous support layer, should have sufficient chemical resistance to each of the components in the spent solvent or operative fluid.

Components of the membrane may be comprised of an inorganic material, e.g., glass, ceramic, sintered metal, or the like (especially as supports), or organic material, i.e., polymers. In the case of polymers, both addition and condensation polymers which can be fabricated in any suitable manner to provide membranes, are included. Generally organic, or organic polymers which may be mixed with inorganic materials (e.g., fillers), are used to prepare the membranes. Typical polymers can be substituted or unsubstituted polymers and may be selected from polysulfones, such as bisphenol A polysulfone (sold under the mark "Udel" by Amoco Performance Products, Inc.) or polyether sulfone (sold under the mark "Victrex" by Imperial Chemical Industries); polyacrylonitriles; polyethers; polyamides; polyimides; cellulosic derivatives; poly(arylene oxides) such as poly(phenylene oxide); polyether ketones; polysulfides; polymers from monomers having alpha-olefinic unsaturation other than mentioned above such as poly(ethylene), poly(propylene), poly(butene-1), poly(4-methyl 1-pentene), polyvinyls, e.g., poly(vinyl chloride), poly(vinyl fluoride), poly(vinylidene chloride), poly(vinylidene fluoride), and the like.

The foregoing materials may, for composite membranes, be used for the support, or substrate, or the membrane coating layer. Substrates prepared from polysulfone or polyimide are particularly preferred.

Porous polysulfone or substrates of other material can be prepared in accordance with conventional techniques. For instance, hollow fibers are generally spun from a dope composition of the desired fiber polymer, quenched, washed and dried. As disclosed by Cabasso, et al. in "Composite Hollow Fiber Membranes", Journal Of Applied Polymer Science, Volume 23, 1509-1525 (1979), and in "Research and Development of NS-1 and Related Polysulfone Hollow Fibers for Reverse Osmosis Desalination of Seawater", Gulf South Research Institute, July 1975, distributed by National Technical Information Service, U.S. Department of Commerce Publication PB 248,666, polysulfone hollow fibers can be spun from a ternary solution of polysulfone, poly(vinyl pyrrolidone) and dimethylacetamide, with the total polymeric concentration in the solution desirably being 40 to 52 weight %, and the polysulfone/poly(vinyl pyrrolidone) ratio being 1.5:2.0. The well known tube-in-tube jet technique is disclosed as being suitable for the spinning procedure, with water at about 21° C. being the preferred outside quench medium for the fibers. The quench medium in the center of the fiber is frequently air. Quenching is typically followed by washing the fibers, for example, conveniently with hot water at about 50° to 60° C. Following such washing, the hollow fibers are dried prior to being coated with the membrane coating layer to form the desired composite membrane. For this purpose, the polysulfone hollow fibers are typically dried by passage through a hot air drying column for a suitable period of time.

Hollow fiber substrates are typically substantially porous and the extent of their surface and bulk porosity is influenced by the dry/wet, wet, dry or melt extrusion technique used in their manufacture. The porosity of the hollow fibers may be further modified by solvent annealing or high temperature annealing techniques. Pore-fuming additives can also be used in preparing the membrane substrates and/or coating layers. The pore-fuming additives can be incorporated into the polymer solutions from which the membranes are prepared. Frequently, the pore-fuming additives do not comprise greater than about 30 to 40 weight percent of the solution. Materials which may find application as pore-fuming additives include lower molecular weight organic acids and lower molecular weight dihydric and polyhydric alcohols, e.g., of molecular weights of from 46 to 150 or 200. Preferred pore-fuming agents include diethylene glycol and glycerine.

Advantageously, the membrane coating layer for the composite membranes is in the form of an essentially non-interrupted membrane layer in contact with the porous support layer.

The preferred materials for the membrane coating may include, but are not limited to, interfacial polycondensation polymers, such as polyamides, for example, those that are described in U.S. Pat. Nos. 4,277,344 and 4,830,885, the contents of which are incorporated herein by reference.

Also preferred materials for the membrane coating include polymers having pendant anionic groups. Often, the anionic groups are present in a concentration such that the ion exchange capacity of the membrane is from about 0.01 to about 3 milliequivalents per gram of dry polymer, preferably from about 0.5 to about 2 milliequivalents per gram of dry polymer.

Most preferably, a sulfonated polysulfone is utilized as the membrane coating material for the composite membrane. Such sulfonated polysulfones are discussed in, for example, U.S. Pat. Nos. 3,709,841, 4,054,707, 4,207,182, European Patent Application 0,202,849, European Patent Application 0,165,077 and European Patent Application 0,202,841 all of which are incorporated herein by reference as if set out in full. Sulfonated-polysulfones are also discussed in the Journal of Applied Polymer Science, Volume 20, pages 1885-1903 (1976) in an article entitled *Sulfonated Polysulfone* by A. Noshay, et al., the contents of which are also incorporated herein by reference. Sulfonated polyarylether sulfones and sulfonated polyetherether sulfones and reverse osmosis membranes made therefrom are disclosed in U.S. Pat. Nos. 4,414,368; 4,508,852; 4,268,650; and 4,273,903, which are also incorporated herein by reference. Methods of preparation of sulfonated polyether ketones and salts thereof can be found in an article by Xigao Jin, et al., British Polymer Journal, Vol. 17, pp. 4-10, (1985). Preparation of asymmetric sulfonated polyether ketone reverse osmosis membranes from sulfonated polyether ketones is described in U.S. Pat. No. 4,714,725, incorporated herein by reference.

Polyarylether sulfone with at least one sulfonic acid group present on one of the aromatic rings is one of the more common sulfonated polysulfones which is applicable in the present invention. Sulfonated bisphenol A polysulfone is particularly preferred as the coating for the separation layer for the composite membrane.

The sulfonation of polysulfone can be carried out in accordance with the procedures described in, for example, U.S. Pat. No. 3,709,841. Suitable sulfonating reagents include chlorosulfonic acid ($ClSO_3H$) which is a preferred sulfonating agent. However, it is also possible to use, for example, sulfur trioxide and its addition products with Lewis bases containing oxygen as the electron donor atom; sulfuric acid and fuming sulfuric acid can also be used. The sulfonation reaction is generally carried out at $-50°$ to $+80°$ C., preferably at $-10°$ to $+35°$ C., in solution in a solvent for the polyarylether sulfone which is inert as regards the sulfonation reaction. Halogenated hydrocarbons, especially methylene chloride, 1,2-dichloroethane and 1,1,2,2-tetrachloroethane are suitable solvents.

The amount of sulfonating agent employed is generally such that the ratio of the number of sulfur atoms of the sulfonating agent to the number of sulfur atoms of the non-sulfonated polyaryl-ether-sulfone is from about 0.3 to about 6, and preferably from about 1.2 to 4. The exact number of sulfonic groups which can be fixed to the non-sulfonated polyaryl-ether can of course be altered by adjusting the sulfonation conditions and, in particular, the temperature, the duration of the reaction, and the concentration of the reagents. The sulfonated polyaryl-ether-sulfone produced can be isolated in accordance with the method described in, for example, U.S. Pat. Nos. 3,709,841 or 3,875,096.

Other methods for the preparation and isolation of a sulfonated polysulfone can be adopted to prepare such sulfonated polysulfones.

Sulfonated polyarylethersulfones with degrees of substitution between about 1.0 to about 2.5 meq/g of dry polymer that are soluble in solvents such as methoxyethanol, nitromethane, and alcohol/water mixtures are particularly useful for the preparation of the composite membranes.

The dried membrane support, or substrate, is typically coated with the membrane coating solution of the sulfonated-polysulfone or other membrane material and is then dried. Such a coating and drying sequence may comprise the technique used and described by Coplan, et al., U.S. Pat. No. 4,467,001, which is incorporated herein by reference. Thus, the dried substrate is passed through the membrane coating solution contained in a coating vessel and is then passed through a drier oven and a cure oven. In the ovens, the composite membrane is contacted with drying air or other suitable gas and then the higher temperature curing air or other gas. The membrane is then taken up on a winder or otherwise being processed or stored for eventual incorporation in membrane modules suitable for use in the desired separation operation. For coating with the sulfonated polysulfone, drying temperatures of from about 50° C. to about 130° C. are generally used. Those skilled in the art will appreciate that it is also possible to dry the membrane coating layer on the support layer without employing the separate curing step.

The membranes are generally assembled as part of a membrane separating device (or module). The membrane device is designed to carry out a selective separation of at least one component from a fluid stream mixture. The membrane apparatus will typically consist of an enclosure and a membrane assembly positioned therein. The membrane assembly can be constructed in the form of a spiral wound cartridge, a hollow fiber bundle, a pleated flat sheet membrane assembly, and like assemblies. The membrane assembly is constructed so as to have a feed-surface side and an opposite permeate exit side. The enclosure is constructed so as to enable the feed stream mixture to be brought into contact with the membrane feed-surface side. Conduit means are provided for the removal of the part of the feed stream that did not permeate through the membrane, and for the separate removal of the permeate components that have passed through the membrane.

Reverse osmosis is the means by which the liquid separation of the present invention is carried out. In conducting the liquid separations, including concentrations, of the present invention, the exit side of the membrane is maintained at a pressure which is less than the pressure at the feed side. The driving force for the desired permeation through the membrane is a differential in the pressure drop across the membrane. Permeating components, e.g., ethylene glycol and water (if present), pass into and through the membrane and can be removed from the vicinity of the exit side of the membrane to maintain the desired driving force for the permeation. Typically, the operation of the membrane does not depend upon the direction of feed flow or the surface of the membrane which is first contacted by the feed.

The feed sent to the membrane separator can be supplied to the membrane separator at a pressure in the range of from about 10 to about 2000 pounds per square inch gauge (psig), preferably in the range of from about 50 to about 1500 psig, and most preferably in the range of from about 200 to about 1000 psig. The permeate pressure is generally maintained between about ambient pressure to about 2000 psig, although lower or higher permeate pressures may find utility.

The temperature of the feed can vary from below ambient to about 120° C., generally about 10° to about 100° C., and preferably about 15° to about 95° C.

The reverse osmosis may be conducted on a batch or, preferably, continuous basis. Often, the contact time of the feed with the membrane is sufficient so that at least about 50 volume percent of the lower glycol in the feed permeates the membrane. For instance, about 50 to 98, say, about 60 to 95, volume percent of the lower glycol in the feed permeates. Generally, the amount of the lower glycol that is permeated is determined based upon the amount of impurities that can be tolerated in the reclaimed lower glycol. The rate at which an impurity passes through a membrane depends upon the nature of the impurity and its permeation coefficient in the material of the membrane and the concentration of the impurity in the feed.

The reverse osmosis system may comprise one or more stages. When using a plurality of stages, common configurations include feed side staging and permeate side staging. In feed side staging, the rejected fluid from one stage is passed to the feed side of another stage and further lower glycol recovery is obtained. In permeate side staging, the permeate from one stage is passed to the feed side of another stage to achieve further purification.

Since many of the impurities contained in operative fluids containing lower glycol are ionic in nature, the electroconductivity of the permeate can be used as a measure of purity of the reclaimed lower glycol. At 25° C., the electroconductivity of a 50 percent aqueous solution of lower glycol with distilled water is about 1.2 micromhos (microsiemens). Advantageously, the reclaimed lower glycol from the processes of this invention has, at 25° C. in 50 percent aqueous solution, an electroconductivity no more than about 0.5, say, less than about 0.3, of that of the feed under the same concentration and at the same temperature. Generally, the reclaimed lower glycol under these conditions has an electroconductivity less than about 10, say, less than about 5, e.g., between about 0.002 to 3, millimho (millisiemens).

As discussed above, operating procedures can be used which enhance the useful life of membranes to reclaim lower glycol. One technique is to maintain sufficient diluent, preferably water, on the feed side of the membrane to assure that the membrane is not unduly deleteriously affected by the lower glycol. Often, operative fluids from which lower glycol is to be reclaimed already contain water. However, if insufficient water is present, water may be added to the feed. Water will typically permeate the membrane and thus be present with the lower glycol permeate. If desired, the water can be removed by distillation which, because of the boiling point difference between water and lower glycol, can be facilely accomplished without undue energy consumption or risk of degradation of lower glycol. Often, the combination of lower glycol on the feed side of the membrane is less than about 80 volume percent based on the volume of feed. Typically, the concentration of water in the feed to the membrane is at least about 10, e.g., at least about 15 or 20, say, about 15 to 80 volume percent based on the total volume of the feed.

Another technique for enhancing the stability of a membrane used for liquid separations, especially membranes having pendant anionic groups, is by continuously or periodically contacting the membrane with a solution containing divalent and/or polyvalent cations, preferably comprising divalent cations, in an amount sufficient to enhance the stability of the membrane. When the contact is continuous, the stabilizing cation is often present in an amount of about 1 to 250, say, about 5 to 100, parts per million by weight. The periodic contacting is generally accomplished with more concentrated solutions of cation, e.g., often the salt providing the stabilizing cation is in at least a 0.01 Normal solution in solvent, e.g., water, but the concentration of the salt is less than the saturation point under the conditions of the treatment. Frequently, the salt solution is between about 0.1 and 2 Normal. The anion associated with the cation should enable sufficient solubility of the cation in the solution to provide the stabilizing effect. Often the cation is halide, carbonate, sulfate, nitrate, carboxylate (e.g., acetate) or phosphate. The treating solution may be substantially the same as the feed, or may be aqueous. When the contacting is intermittent, the contacting generally occurs for a period of at least about 0.5 minute, e.g., about 0.1 to 100, preferably about 0.1 to 50, hours. While the stabilization method is useful for the recovery of lower glycols from operative fluids, it can have much wider utility to virtually all liquid separations by reverse osmosis, especially using anionic group-containing membranes.

In an aspect of the invention, the operative fluid containing lower glycol may be subject to filtration prior to being fed to the membrane, e.g., to remove particles and debris which may otherwise adversely affect the membrane. Often, the filtration removes particles and debris having an effective particle size for filtration of greater than about 5, say, greater than about 1, and sometimes even greater than about 0.1, microns.

The following examples are in further illustration but not in limitation of the invention. All parts and percentages of solids are by weight and of fluids, by volume, unless otherwise indicated.

EXAMPLES

In the following examples, the units used to describe the results obtained are defined as follows.

"Stage Cut" is a measure of how much feed the separator module can treat. It is defined as the ratio of permeate flowrate to the feed flowrate. The higher the stage cut, the higher the ethylene glycol recovery and the higher the concentration of impurities in the raffinate.

"% Rejection" is a measure of how much of a particular solute is rejected by the membrane such that it remains in the raffinate. As used herein, it is defined as:

(Conc. of solute in feed − Conc. of solute in permeate)
* 100/(Conc. of solute in feed)

Except where indicated, the concentration of the salts in either the feed or permeate is measured in terms of its electrical conductivity (milli mho).

"MEG" is monoethylene glycol.

"DEG" is diethylene glycol.

Ideally, the reverse osmosis separation should combine a high solute rejection with a large permeation rate for a large stage cut.

For the test results shown in the following tables, the particular membranes utilized are described therein.

Conductivity measurements were made with a platinum cell, using a digital conductivity meter Model N-01481-90 available from Cole Parmer Instrument Company, Chicago, Ill.

Table I sets forth the composition of used antifreeze compositions which are used in the examples. The antifreeze is fed at a temperature of about 22° to 25° C. and pressure of about 500 psig to the outside hollow fiber membrane contained in a module. The hollow fibers are composed of porous polysulfone having a coating of sulfonated polysulfone about 0.5 micron in thickness and the sulfonated polysulfone has an ion exchange capacity of 1.9 milliequivalents per gram. The module contains about 0.06 square feet of membrane surface area. The hollow fibers in each module are eight hollow fibers about 16 inches in length looped with their ends potted in an epoxy plug. The bundle is housed in a stainless steel shell. The membranes differ in the amount of heat curing. Heat curing is effected between 80° C. and 160° C. and for a time to provide the sought degree of salt rejection. Table II describes the details of each membrane module. Membrane module A exhibits a rejection of the eight mole ethoxylate of nonylphenol (NP-8 available from Union Carbide Chemicals and Plastics Company Inc.) of about 98 percent using a 1 percent aqueous solution feed at Standard Conditions.

In the examples 1 to 6 the permeate sides of the membranes are at ambient laboratory conditions, i.e., essentially atmospheric pressure at about 22° to 25° C. Prior to using the membranes they are soaked in a 0.5 weight percent sodium chloride solution in distilled water. Table III summarizes the results.

TABLE I

|  | Used Antifreeze | |
| --- | --- | --- |
|  | A | B |
| Ethylene glycol | 52.6% | 45.0% |
| Diethylene glycol | 1.17% | 1.4% |
| Water | Balance | Balance |
| Anions |  |  |
| Acetate | 49.9 ppm | 175 ppm |
| Glycolate | 870.9 ppm | 3040 ppm |
| Formate | 169.6 ppm | 365 ppm |
| Metals |  |  |
| Boron | 360 ppm | 197 ppm |
| Copper | 1.7 ppm | 2 ppm |
| Iron | nd | nd |
| Potassium | <9 ppm | 1130 ppm |
| Sodium | 2450 ppm | 1630 ppm |
| Phosphorus | 623 ppm | 190 ppm |
| Silicon | 40 ppm | 27 ppm |
| Triazoles |  |  |
| Antifoaming agent (polyglycol) |  |  |
| Dye |  |  |
| pH | n.a. | 8.4 | nd: not detected
na: not available

TABLE II

| | Sea Water Evaluation | | | |
| --- | --- | --- | --- | --- |
| Membrane Module | Approximate Wall Thickness (mils) | Water Flux gal/ft²/day | Salt Rejection (%) | Ion Exchange Capacity, meq/g dry resin |
| A | 5.5 | 7.1 | 93.9 | 1.9 |
| B | 5.6 | 3.5 | 97.8 | 1.9 |
| C | 5.7 | 1.8 | 99.04 | 1.9 |

TABLE III

| Example | Membrane | Antifreeze Type | Time on Stream (hours) | Permeate (ml/hr) | Stage Cut (%) | Permeate Conduc. (milli mho) | Salt Rejection (%) | Rejection MEG (%) | Rejection DEG (%) |
| --- | --- | --- | --- | --- | --- | --- | --- | --- | --- |
| 1 | A | A | 0 | 9.0 | 1.5 | 0.94 | 52.3 | | |
|   |   |   | 5 | 15.0 | 2.9 | 1.25 | 39.3 | | |
| 2 | B | B | 0 | 11.2 | 0.2 | 0.75 | 75.5 | 0.9 | 2.1 |
|   |   |   | 43 | 43.0 | 0.7 | 2.23 | 36.6 | 2.5 | 7.2 |
| 3 | B | B | 17 | 27.0 | 0.5 | 1.53 | 50.7 | 0.4 | 6.9 |
|   |   |   | 41 | 30.0 | 0.6 | 1.71 | 47.1 | 0.0 | 6.7 |
|   |   |   | 137 | 29.0 | 0.5 | 1.79 | 42.8 | na | na |
| 4 | B | B | 35 | 14.0 | 0.7 | 0.99 | 70.8 | 4 | 20.1 |
|   |   |   | 81 | 13.0 | 0.7 | 1.64 | 64.5 | 0 | 15.1 |
|   |   |   | 272 | 13.0 | 0.7 | 2.46 | 45.8 | −6.4 | 2 |
|   |   |   | 440 | 15.0 | 0.8 | 2.6 | 36 | | |
| 5 | C | B | 35 | 4.0 | 0.2 | 0.42 | 87.6 | 4.7 | 33.3 |
|   |   |   | 272 | 3.0 | 0.2 | 0.84 | 81.5 | −6.7 | 14.7 |
|   |   |   | 440 | 5.0 | 0.3 | 1.04 | 74.4 | na | na |
| 6 | C | B | 35 | 4.0 | 0.2 | 0.4 | 88.2 | 9.1 | 30.9 |
|   |   |   | 272 | 3.0 | 0.2 | 0.73 | 83.9 | −7.1 | 15.3 |
|   |   |   | 440 | 4.5 | 0.2 | 0.84 | 79.3 | na | na | na = not available

Twelve membrane modules are prepared. Eight modules use the same type of membrane (D) used in module A. Four modules use a similar membrane (E) but have a Water Flux of 2.2 gal/ft²/day, a salt rejection of about 99.09 percent and an ion exchange capacity of about 1.9 milliequivalents per gram of dry resin. These four modules are used for the experiments with magnesium counterion. The remaining eight are used for the experiments with sodium and iron counterions. Prior to using the membranes, they are soaked in a salt solution containing the designated counterion. The sodium counter ion-containing membranes are prepared by soaking for about 2 to 4 days in a 0.5 weight percent sodium chloride solution in distilled water. The magnesium counter ion-containing membranes are prepared by soaking for about 10 days in a distilled water solution containing 25 weight percent magnesium sulfate heptahydrate. Two of the membrane modules are soaked for about 10 days in a solution of 1 weight percent ferric sulfate in distilled water. These modules are used for the experiments reported in Table IV. Two of the modules are soaked for about 10 days in a solution of 0.5 weight percent ferric sulfate in distilled water. These modules are used for the experiments reported in Table V.

Six modules are soaked in a solution of 50 volume percent monoethylene glycol, except as indicated in Table IV. Periodically, the modules are removed from the soaking medium and used to treat a 0.5 weight percent sodium chloride aqueous solution at about 25° C. and 430 pounds per square inch gauge feed pressure, ambient permeate pressure and at stage cuts of less than five percent. The results are summarized in Table IV.

Six modules are soaked in used antifreeze B except as indicated in Table V. Periodically, the modules are removed from the soaking medium and used to treat a 0.5 weight percent sodium chloride aqueous solution at about 25° C. and 430 pounds per square inch gauge feed pressure, ambient permeate pressure and at stage cuts of less than five percent. The results are summarized in Table V. As can be seen, the performance of the membrane is improved in the the presence of the divalent and polyvalent cations.

TABLE IV

| Membrane | Membrane Counterion | Soaking Time (days) | Permeate (ml/hr) | Permeate Conductivity (millimho) | Salt Rejection (%) |
| --- | --- | --- | --- | --- | --- |
| D | Na+ | 0 | 19 | 0.43 | 95.4 |
|   |   | 25 | 54 | 3.7 | 64 |
|   |   | 42 | 60 | 5.1 | 48.3 |
|   |   | 81 | 62 | 5.9 | 39.1 |
|   |   | 94 | 54 | 6.3 | 40.2 soaked 0.5% NaCl |
|   |   | 119 | 38 | 4.8 | 52.6 soaked in 0.5% NaCl |
| D | Na+ | 0 | 20 | 0.44 | 95.3 |
|   |   | 42 | 88 | 5.4 | 42.6 |
|   |   | 81 | 112 | 7.6 | 29.1 |
|   |   | 94 | 64 | 7.2 | 36.3 soaked in 0.5% NaCl |
|   |   | 119 | 56 | 4.7 | 53.1 soaked in 0.5% NaCl |
| E | Mg++ | 0 | 10 | 0.51 | 95.3 |
|   |   | 5 | 16 | 1.68 | 86 |
|   |   | 19 | 13 | 0.85 | 90.2 soaked in 25% MgSO$_4$.7H$_2$O |
|   |   | 27 | 20 | 1.45 | 83.9 |
| E | Mg++ | 0 | 11 | 0.45 | 95.8 |
|   |   | 5 | 20 | 1.09 | 90.9 |
|   |   | 19 | 15 | 0.81 | 90.7 soaked in 25% MgSO$_4$.7H$_2$O |
|   |   | 27 | 22 | 1.22 | 86.5 |
| D | Fe+++ | 0 | 16 | 0.4 | 95.9 |
|   |   | 19 | 25 | 1.3 | 88.9 |
|   |   | 49 | 48 | 3.26 | 70.3 |
|   |   | 70 | 18 | 2.12 | 77.2 soaked in 1% Fe$_2$(SO$_4$)$_3$ |
| D | Fe+++ | 0 | 17 | 1.6 | 83.7 |
|   |   | 19 | 23 | 1.7 | 84.9 |
|   |   | 49 | 66 | 4.6 | 58.4 |

TABLE IV-continued

| Membrane | Membrane Counterion | Soaking Time (days) | Permeate (ml/hr) | Permeate Conductivity (millimho) | Salt Rejection (%) | |
|---|---|---|---|---|---|---|
| | | 70 | 28 | 2.8 | 70 | soaked in 1% $Fe_2(SO_4)_3$ |

In these experiments, the membranes are soaked in 50% MEG in water except when the last column says otherwise. Periodically, the hollow fiber membranes are tested with a 0.5% solution at 430 psi and 25° C.

TABLE V

| Membrane | Membrane Counterion | Soaking Time (days) | Permeate (ml/hr) | Permeate Conductivity (millimho) | Salt Rejection (%) | |
|---|---|---|---|---|---|---|
| D | Na+ | 0 | 19 | 0.3 | 96.6 | |
| | | 25 | 42 | 5.2 | 49.4 | |
| | | 42 | 56 | 6.1 | 38.1 | |
| | | 81 | 60 | 7.7 | 20.5 | |
| | | 94 | 30 | 7.8 | 26.1 | soaked in 0.5% NaCl |
| | | 119 | 28 | 7.7 | 23.6 | soaked in 0.5% NaCl |
| D | Na+ | 0 | 17 | 0.35 | 96.3 | |
| | | 25 | 42 | 3.5 | 67.5 | |
| | | 42 | 40 | 5.2 | 44.4 | |
| | | 81 | 44 | 7.1 | 34.1 | soaked in 0.5% NaCl |
| | | 94 | 22 | 6.7 | 40.7 | soaked in 0.5% NaCl |
| | | 119 | 30 | 7.8 | 22.7 | soaked in 0.5% NaCl |
| E | Mg++ | 0 | 10 | 0.5 | 95.4 | |
| | | 5 | 17 | 1.12 | 90.6 | |
| | | 19 | 13 | 1.26 | 85.5 | soaked in 25% $MgSO_4.7H_2O$ |
| | | 27 | 19 | 1.67 | 81.5 | |
| E | Mg++ | 0 | 10 | 0.68 | 93.4 | |
| | | 5 | 16 | 1.3 | 89.2 | |
| | | 19 | 13 | 1.12 | 87.1 | soaked in 25% $MgSO_4.7H_2O$ |
| | | 27 | 17 | 1.75 | 80.6 | |
| D | Fe+++ | 0 | 17 | 0.39 | 96.1 | |
| | | 38 | 21 | 1.5 | 83.5 | |
| | | 73 | 21 | 1.94 | 79.3 | |
| D | Fe+++ | 0 | 14 | 0.3 | 97.1 | |
| | | 38 | 26 | 1.1 | 88.3 | |
| | | 73 | 25 | 1.2 | 87.2 | |

In these experiments, the membranes are soaked in used antifreeze except when the last column says otherwise. Periodically, the hollow fiber membranes are tested with a 0.5% solution at 430 psi and 25° C.

It is claimed:

1. A process comprising substantially enhancing the stability of a polymeric reverse osmosis membrane in which the membrane comprises a polymer containing pendant anionic groups, by contacting the membrane with a solution containing a stabilizing amount of at least one polyvalent cation.

2. The process of claim 1 in which the pendant anionic groups comprise at least one of carboxylic, sulfonic, sulfinic, phosphonic, and phosphinic groups.

3. The process of claim 1 in which the pendant anionic groups are present in a concentration such that the ion exchange capacity of the membrane is from about 0.01 to about 3 milliequivalents per gram of dry polymer.

4. The process of claim 1 in which the pendant anionic groups are present in a concentration such that the ion exchange capacity of the membrane is from about 0.5 to about 2 milliequivalents per gram of dry polymer.

5. The process of claim 1 in which the membrane comprises sulfonated polysulfone.

6. The process of claim 1 in which the contact with the cation is periodic.

7. The process of claim 6 in which the solution containing the cation has a normality of at least 0.01.

8. The process of claim 1 in which the cation comprises divalent cation.

9. The process of claim 8 in which the divalent cation comprises alkaline earth metal cation.

* * * * *